United States Patent
Wruck et al.

(10) Patent No.: US 6,830,048 B2
(45) Date of Patent: Dec. 14, 2004

(54) GAS MIXER WITH A PLURALITY OF EJECTORS FOR A MEDICAL RESPIRATOR

(75) Inventors: Norbert Wruck, Lübeck (DE); Rainer Kunz, Lübeck (DE); Thomas Rossen, Lübeck (DE); Joachim Schröter, Lübeck (DE)

(73) Assignee: Drager Medical AG & Co., KGaA, Lübeck (DE)

( * ) Notice: Subject to any disclaimer, the term of this patent is extended or adjusted under 35 U.S.C. 154(b) by 27 days.

(21) Appl. No.: 10/306,698

(22) Filed: Nov. 27, 2002

(65) Prior Publication Data

US 2003/0150456 A1 Aug. 14, 2003

(30) Foreign Application Priority Data

Feb. 13, 2002 (DE) .......................................... 102 05 845

(51) Int. Cl.⁷ ................................................. G05B 1/00
(52) U.S. Cl. .............................. 128/205.11; 128/204.18; 128/205.24
(58) Field of Search ...................... 128/200.24, 203.12, 128/203.14, 203.16, 203.25, 204.18, 204.21, 204.22, 205.11, 205.211, 207.12, 207.14, 207.16, 207.18

(56) References Cited

U.S. PATENT DOCUMENTS

| | | | | |
|---|---|---|---|---|
| 3,974,828 A | * | 8/1976 | Bird ....................... | 128/204.25 |
| 4,072,148 A | * | 2/1978 | Munson et al. ........ | 128/205.11 |
| 5,660,171 A | * | 8/1997 | Kimm et al. .......... | 128/204.23 |
| 5,823,186 A | * | 10/1998 | Rossen et al. ......... | 128/204.21 |
| 5,934,274 A | * | 8/1999 | Merrick et al. ........ | 128/203.25 |
| 6,279,574 B1 | * | 8/2001 | Richardson et al. ... | 128/204.18 |

FOREIGN PATENT DOCUMENTS

DE    199 07 362    8/2000

* cited by examiner

*Primary Examiner*—Glenn K. Dawson
(74) *Attorney, Agent, or Firm*—McGlew and Tuttle, P.C.

(57) ABSTRACT

A device and a process for mixing at least a first gas component with a second gas component is suitable for mixing gases in a portable respirator. The gas mixer device makes it possible to bring about the particularly necessary concentration of the first gas component at different volume flows of the gas mixture generated. The gas mixer device has a plurality of ejectors (1, 2) of different sizes, which are designed according to the principle of a venturi nozzle. The ejectors have respective propellant gas connections (3, 9) for feeding the first gas component from a propellant gas container (4) and suction channels (5, 10) for feeding the second gas component from a mixing chamber (6), as well as gas outlets (8, 11) to a respiration connection (7). An evaluating and control unit (17) evaluates the signals of two volume flow sensors (15, 16) and correspondingly actuates proportional valves (13, 14) arranged in the propellant gas connections (3, 9) for feeding the first gas component. For small respiration flows, the proportional valve (13) in the propellant gas connection (3) for the smaller ejector (1) is actuated by the evaluating and control unit (17) for opening, the proportional valve (14) in the propellant gas connection (9) for the larger ejector (2) is actuated for opening in the case of medium respiration flows, and both proportional valves (13, 14) are actuated by the evaluating and control unit (17) for opening for high respiration flows.

9 Claims, 2 Drawing Sheets

GAS MIXER WITH A PLURALITY OF EJECTORS FOR A MEDICAL RESPIRATOR

FIELD OF THE INVENTION

The present invention pertains to a device as well as to a process for mixing at least a first gas component with a second gas component. Such a device can be used especially as a gas mixer in a portable respirator.

BACKGROUND OF THE INVENTION

A device of the type mentioned has been known from DE 199 07 362 A1, in which ambient air is drawn in as a second gas component via a channel by means of a venturi nozzle, through which a propellant gas is led as a first gas component, wherein a partial flow of the first gas component is likewise drawn in via the channel via an additional bypass line. If pure oxygen is used as the propellant gas, an average oxygen concentration arising from the partial flows of the pure oxygen as the first gas component and the ambient air as the second gas component becomes established at the gas outlet of the venturi nozzle. Due to the fact that the pure oxygen as a propellant gas is the first gas component, it is utilized optimally, and the volume of the pressurized gas cylinder for the oxygen can be kept as small as possible.

The fact that the oxygen concentration in the gas mixture can be changed to a limited extent only proved to be a drawback of the prior-art device. For example, the gas mixture has a higher oxygen concentration than necessary during the respiration of infants or during respiration with high volume flows. In the first case the ejector cannot produce a sufficient suction flow for fluid dynamic reasons and in the second case the necessary high volume flow can be generated only by the increased inflow of oxygen from the pressurized gas cylinder.

SUMMARY OF THE INVENTION

The object of the present invention is to provide a device and a process for mixing at least two gas components such that the particularly necessary concentration of the first gas component can be brought about at different volume flows of the gas mixture generated as a result.

The device and the process are suitable for mixing at least a first gas component with a second gas component. The device has a plurality of ejectors of different sizes, which are designed according to the principle of a venturi nozzle. A propellant gas flow of up to 5 liters per minute (L/minute) and a suction flow of up to 30 liters per minute (L/minute) can be generated with a smaller ejector, and a propellant gas flow of up to 10 liters per minute (L/minute) and a suction flow of up to 60 liters per minute (L/minute) can be generated with a larger ejector. Liters per minute (L/minute) always means hereinafter normal liters per minute (NL/minute) in order to indicate a variable that is independent from the pressure and the temperature. The ejectors have propellant gas connections for feeding the first gas component from a propellant gas container and suction channels for feeding the second gas component from a mixing chamber, as well as gas outlets to a respiration connection. The mixing chamber itself is supplied with the second gas component via a central suction channel. Proportional valves, which regulate the feed of the first gas component via the propellant gas connections, are arranged in the propellant gas connections. A volume flow sensor each is arranged in the central suction channel for the second gas component and directly before the respiration connection. The first volume flow sensor in the central suction channel measures the volume flow of the second gas component, and the second volume flow sensor directly before the respiration connection measures the volume flow of the gas mixture consisting of all the gas components.

The volume flow sensors and the proportional valves are connected via lines to an evaluating and control unit, which evaluates the signals of at least the second volume flow sensor and correspondingly actuates the proportional valves. In the case of a signal of up to about 20 liters per minute (L/minute) to be measured by the second volume flow sensor, the first proportional valve before the smaller ejector is actuated for opening by the evaluating and control unit. In the case of a signal to be measured between about 20 liters per minute (L/minute) and about 45 liters per minute (L/minute), the evaluating and control unit actuates the second proportional valve before the larger ejector for opening, and in the case of a signal to be measured above 45 liters per minute (L/minute), both proportional valves are actuated for opening.

To ensure that the second gas component always reaches the ejectors via the suction channels, nonreturn valves, which prevent gas components from an ejector that is not in operation because of the closed proportional valve arranged upstream in the corresponding propellant gas connection from reaching the other ejector via the mixing chamber or the central suction channel for the second gas component, are arranged in all suction channels in a preferred embodiment.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
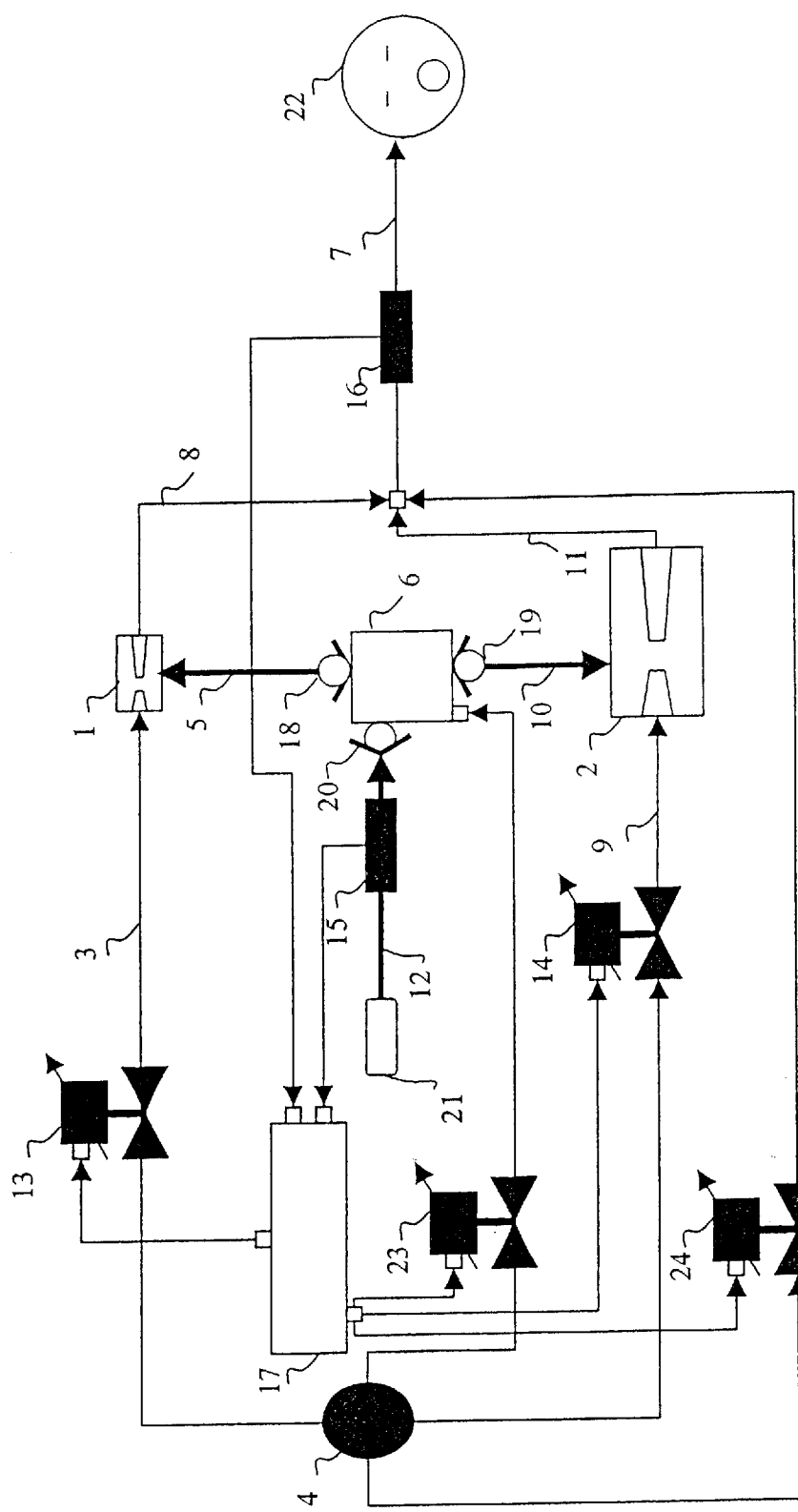
FIG. 1 is a schematic view showing a device according to the present invention for mixing at least two gas components.

Referring to the drawings in particular, FIG. 1 schematically shows a device according to the present invention for mixing at least two gas components. Oxygen is used as the first gas component, and ambient air 21 is used as the second gas component. The oxygen is taken from a propellant gas container 4. The device for mixing oxygen and ambient air 21 has two ejectors; a smaller ejector 1 and a larger ejector 2. The oxygen flows from the propellant gas container 4 via a first propellant gas connection 3 to the smaller ejector 1, which operates according to the principle of a venturi nozzle and draws in the ambient air 21 from a mixing chamber 6 via a first suction channel 5. Via a second propellant gas connection 9, the oxygen flows from the propellant gas container 4 to the larger ejector 2, which has the same design as the smaller ejector 1. The larger ejector 2 draws in the ambient air 21 from the mixing chamber 6 via a second suction channel 10. The mixing chamber 6 is in turn supplied with the ambient air 21 via a central suction channel 12. A first gas outlet 8 leads from the smaller ejector 1 to a respiration connection 7 for a patient 22 connected thereto, and a second gas outlet 11 leads from the larger ejector 2 to the respiration connection 7. The smaller ejector 1 has an internal diameter between 0.3 mm and 0.5 mm, as a result of which a propellant oxygen gas flow of up to 5 liters per minute (L/minute) and a suction flow of the ambient air of up to 30 liters per minute are generated. The larger ejector 2 has an internal diameter between 0.4 mm and 0.7 mm, as a result of which a propellant oxygen flow of up to 10 liters per minute and a suction flow of the ambient air of up to 60 liters per minute are generated. The feed of oxygen from the propellant gas container 4 via the first propellant gas connection 3 is regulated by means of a first proportional valve 13 located therein. A corresponding second proportional valve 14 is located in the second propellant gas connection 9. A third proportional valve 23 is arranged in a connection line between the propellant gas container 4 and the mixing chamber 6. Furthermore, a fourth proportional valve 24 is located in a connection line between the propellant gas container 4 and the respiration connection 7. Furthermore, a first volume flow sensor 15 is located in the central suction channel 12, and a second volume flow sensor 16 is located in the respiration connection 7 to the patient 22. The signals measured by the volume flow sensors 15 and 16 are sent to an evaluating and control unit 17, which in turn controls the opening and closing of the proportional valves 13 and 14 as well as 23 and 24. A first nonreturn valve 18, which is to prevent a gas volume flow from the smaller ejector 1 to the mixing chamber 6, is located in the first suction channel 5. A second nonreturn valve 19 in the second suction channel 10 correspondingly prevents a gas volume flow from the larger ejector 2 to the mixing chamber 6, and a third nonreturn valve 20 in the central suction channel 12 correspondingly prevents a gas volume flow from the mixing chamber 6 to the ambient air 21. The third proportional valve 23 and the fourth proportional valve 24 can be actuated by the evaluating and control unit 17 for opening when more oxygen is needed in the gas volume flow through the respiration connection 7.

Figure 2:
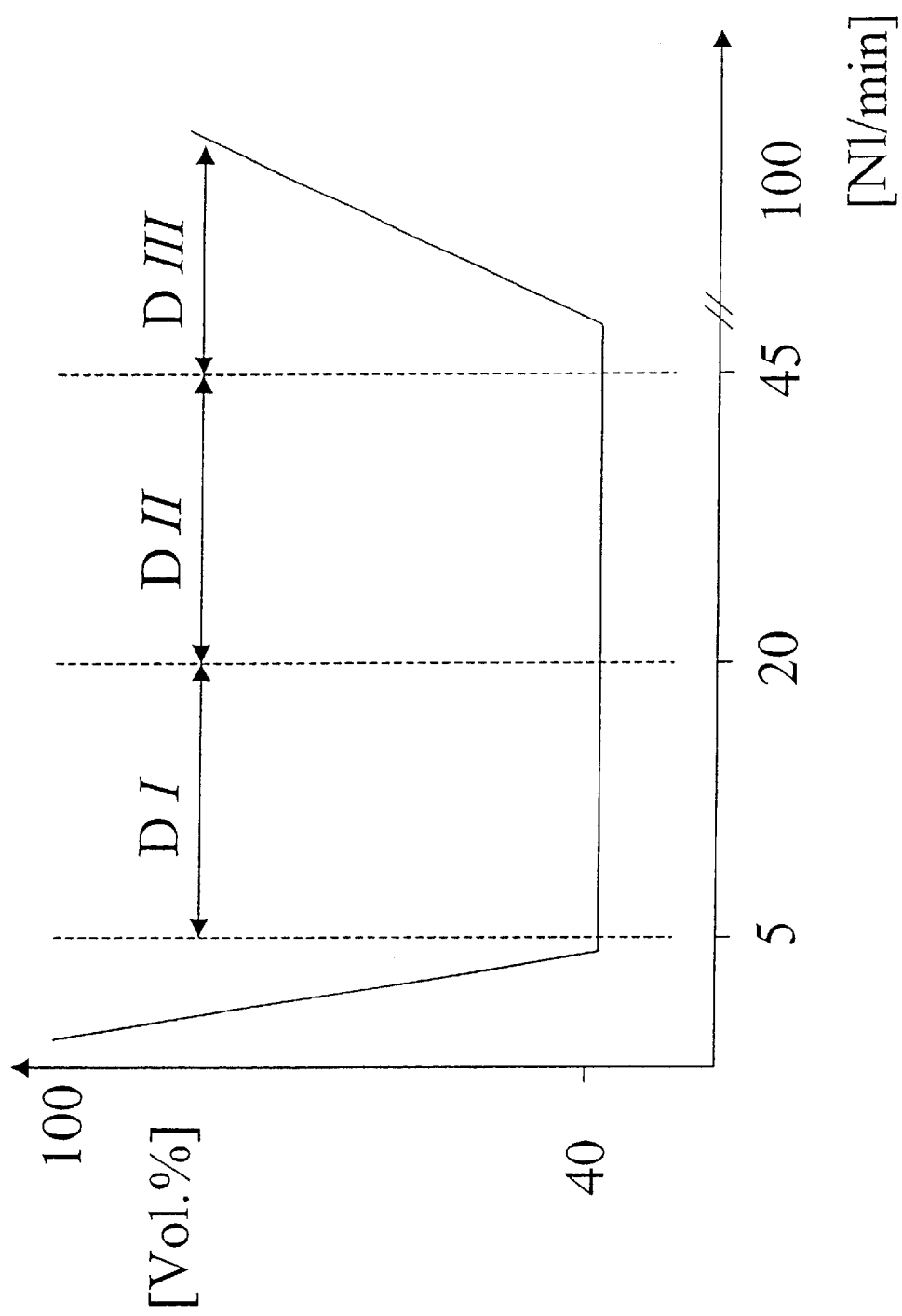
FIG. 2 is a diagram showing the measured inspiratory oxygen content, plotted as a function of the volume flow at the respiration connection of the device from FIG. 1 for mixing at least two gas components.

The mode of operation of the device according to FIG. 1 will be explained on the basis of FIG. 2. FIG. 2 shows the measured inspiratory oxygen content, plotted as a function of the volume flow at the respiration connection 7 of the device shown in FIG. 1 for mixing at least two gas components. The inspiratory oxygen content is shown on the ordinate in volume percent (vol. %). It is determined by forming first the difference between the signal determined by the first volume flow sensor 15 and the signal determined by the second volume flow sensor 16. The first volume flow sensor 15 measures the volume flow of the ambient air 21 through the central suction channel 12, and the second volume flow sensor 16 measures the volume flow generated by the mixture of oxygen from the propellant gas container 4 and the ambient air 21. The volume flow of the oxygen from the propellant gas container 4, which reaches the patient through the respiration connection 7, is determined indirectly from the difference of the signals of the volume flow sensors 15 and 16. From this information to obtain the inspiratory oxygen content in the gas volume flow through the respiration connection 7 to the patient 22, the natural oxygen content in the ambient air 21 must first be taken into account. The two components together, both the oxygen from the propellant gas container 4 and the oxygen of the ambient air 21, determine the inspiratory oxygen content at the respiration connection 7. The volume flow through the respiration connection 7 is plotted in liters per minute (L/minute) and is divided into sections DI, DII and DIII, which are separated from each other by vertical broken lines. Section DI comprises volume flows between 5 and 20 L/minute, and it indicates the dosage range for infants. Section DII comprises the range of 20 to 45 L/minute and is considered the normal case. Section DIII is that of volume flows of more than 45 L/minute, which occur as peak values during extreme spontaneous respiration. In range DII, which is used most frequently, it is possible to bring the inspiratory oxygen content to the desired 40 vol. % due to the dimensioning of the larger ejector 2 described in FIG. 1. Range DI can likewise be covered by the dimensioning of the smaller ejector 1 described in FIG. 1, and the simultaneous actuation of both ejectors 1 and 2 makes it possible to generate very large volume flows in range DIII. A signal of up to 20 L/minute to be measured by the second volume flow sensor 16 in range DI is evaluated by the evaluating and control unit 17 in such a way that the first proportional valve 13 is actuated for opening in this case and the second proportional valve 14 remains closed. In the case of a signal between 20 L/minute and 45 L/minute, which is to be measured by the second volume flow sensor 16, the second proportional valve 14 is actuated by the evaluating and control unit 17 for opening, and the first proportional valve 13 remains closed. In the case of a signal higher than 45 L/minute in range DIII, which is to be measured by the second volume flow sensor 16, both proportional valves 13 and 14 are actuated by the evaluating and control unit 17 for opening.

While a specific embodiment of the invention has been shown and described in detail to illustrate the application of the principles of the invention, it will be understood that the invention may be embodied otherwise without departing from such principles.

What is claimed is:

1. A device for mixing at least a first gas component with a second gas component, the device comprising:

a respiration connection;

a propellant gas container;

a mixing chamber;

a plurality of ejectors including a smaller ejector with a propellant gas flow of up to 5 liters per minute and with a suction flow of up to 30 liters per minute, said smaller ejector having a first propellant gas flow connection for feeding the first gas component from the propellant gas container, a first suction channel for feeding the second gas component from said mixing chamber, and a first gas outlet leading to said respiration connection, and said plurality of ejectors including a larger ejector with a propellant gas flow of up to 10 liters per minute and with a suction flow of up to 60 liters per minute, said larger ejector having a second propellant gas connection for feeding the first gas component from said propellant gas container, a second suction channel for feeding the second gas component from said mixing chamber and a second gas outlet leading to said respiration connection;

a central suction channel for feeding the second gas component to said mixing chamber;

a first proportional valve regulating a gas feed of a propellant gas connection to said propellant gas container;

a second proportional valve regulating a gas feed of another propellant gas connection to said propellant gas container;

a first volume flow sensor arranged in said central suction channel;

a second volume flow sensor arranged directly before said respiration connection; and an evaluating and control unit actuating said first proportional valve for opening in the case of a signal of up to about 20 liters per minute to be measured by the second volume flow sensor and actuating said second proportional valve for opening in the case of a signal to be measured between about 20 liters per minute and about 45 liters per minute, and actuating both said first proportional valve and said second proportional valve for opening in the case of a signal to be measured above about 45 liters per minute.

2. A device in accordance with claim 1, further comprising:

a first nonreturn valve arranged in said first suction channel;

a second nonreturn valve arranged in said second suction channel; and a third nonreturn valve arranged in said central suction channel.

3. A device in accordance with claim 1, further comprising:

a third proportional valve arranged in a connection line between said propellant gas container and said respiration connection.

4. A device in accordance with claim 2, further comprising:

a third proportional valve arranged in a connection line between said propellant gas container and said mixing chamber.

5. A device in accordance with claim 2, further comprising:

a third proportional valve arranged in a connection line between said propellant gas container and said respiration connection.

6. A device in accordance with claim 1, further comprising:

a third proportional valve arranged in a connection line between said propellant gas container and said mixing chamber.

7. A device in accordance with claim 6, further comprising:

a fourth proportional valve arranged in a connection line between said propellant gas container and said respiration connection.

8. A process for mixing at least a first gas component with a second gas component, the process comprising:

actuating a first proportional valve in a first propellant gas connection by an evaluating and control unit for opening, so that the first gas component is sent from a propellant gas container via the first propellant gas connection through a smaller ejector at a propellant gas flow rate of up to 5 liters per minute and at a suction flow rate of up to 30 liters per minute, and the second gas component is drawn in by the smaller ejector from a mixing chamber via a first suction channel, and the two gas components are sent from the smaller ejector via a first gas outlet to a respiration connection when a volume flow sensor arranged directly before the respiration connection measures a volume flow of up to about 20 liters per minute;

actuating a second proportional valve in a second propellant gas connection by the evaluating and control unit for opening, so that the first gas component is sent from the propellant gas container via the second propellant gas connection through a larger ejector at a propellant gas flow rate of up to 10 liters per minute and at a suction flow rate of up to 60 liters per minute, and the second gas component is drawn in from the mixing chamber via a second suction channel by the larger ejector, and the two gas components are sent from the larger ejector via a second gas outlet to the respiration connection when the volume flow sensor measures a volume flow between about 20 liters per minute and about 45 liters per minute; and actuating both said proportional valves by the evaluating and control unit for opening when the volume flow sensor measures a volume flow of more than about 45 liters per minute.

9. A process for mixing at least a first gas component with a second gas component, the process comprising:

when the flow is to be below about 20 liters per minute actuating a first proportional valve in a first propellant gas connection using an evaluating and control unit so that the first gas component is sent from a propellant gas container via the first propellant gas connection through a smaller ejector at a propellant gas flow rate of up to 5 liters per minute and at a suction flow rate of up to 30 liters per minute, and the second gas component is drawn in by the smaller ejector from a mixing chamber via a first suction channel, and the two gas components are sent from the smaller ejector via a first gas outlet to a respiration connection;

when the flow is to be between about 20 liters per minute and about 45 liters per minute actuating a second proportional valve in a second propellant gas connection by the evaluating and control unit for opening, so that the first gas component is sent from the propellant gas container via the second propellant gas connection through a larger ejector at a propellant gas flow rate of up to 10 liters per minute and at a suction flow rate of up to 60 liters per minute, and the second gas component is drawn in from the mixing chamber via a second suction channel by the larger ejector, and the two gas components are sent from the larger ejector via a second gas outlet to the respiration connection; and when the flow is to be more than about 45 liters per minute actuating both said proportional valves by the evaluating and control unit for opening.

* * * * *